United States Patent [19]

Mochizuki et al.

[11] Patent Number: 5,663,172
[45] Date of Patent: Sep. 2, 1997

[54] PREVENTIVE AGENT FOR PLATELET AGGREGATION

[75] Inventors: Nobuo Mochizuki; Shuichi Souma; Takayoshi Sasaki; Yukihiro Kanaguchi; Nobuhiro Umeda, all of Kanagawa, Japan

[73] Assignee: Nippon Soda Co., Ltd., Tokyo, Japan

[21] Appl. No.: 428,072

[22] PCT Filed: Oct. 22, 1993

[86] PCT No.: PCT/JP93/01527

§ 371 Date: Apr. 26, 1995

§ 102(e) Date: Apr. 26, 1995

[87] PCT Pub. No.: WO94/09784

PCT Pub. Date: May 11, 1994

[30] Foreign Application Priority Data

Nov. 2, 1992 [JP] Japan .................................. 4-317739
Dec. 10, 1992 [JP] Japan .................................. 4-352151

[51] Int. Cl.⁶ .................................................. A61K 31/50
[52] U.S. Cl. ...................................... 514/247; 544/234
[58] Field of Search ....................................... 514/247

[56] References Cited

U.S. PATENT DOCUMENTS 5,110,925 5/1992 Kusase et al. ......................... 514/247

FOREIGN PATENT DOCUMENTS 2-56468   2/1990  Japan.
94-09784  11/1994 WIPO.

*Primary Examiner*—Donald G. Daus
*Attorney, Agent, or Firm*—Jacobson, Price, Holman & Stern, PLLC

[57] ABSTRACT

A preventive agent for platelet aggregation comprising a compound represented by the following general formula [I]:

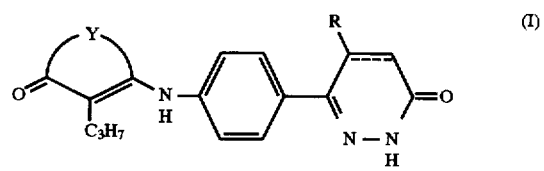

wherein Y is $-CH_2CH_2-$ or $-CH_2CH_2CH_2-$, R is hydrogen or methyl, and ---------- represents a single bond or a double bond, or a pharmaceutically-compatible complex thereof as the active ingredient, is disclosed.

1 Claim, No Drawings

PREVENTIVE AGENT FOR PLATELET AGGREGATION

This application is a Section 371 or PCT/JP93/01527 filed Oct. 29, 1993 published as WO94/09784, May 11, 1994.

FIELD OF THE INVENTION

The present invention relates to a preventive agent for platelet aggregation.

BACKGROUND ART

In Japanese Patent Laid-opened No. Hei 2-56468, compounds represented by the following general formula [II]:

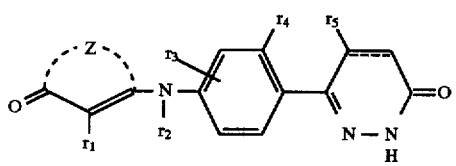

wherein Z is alkylene containing 1 to 4 carbons and optionally substituted by alkyl, lower alkoxy, lower alkylthio lower alkyl, lower alkoxycarbonyl or benzyl, or a group represented by a general formula —C($r_6$) =C($r_7$)— wherein $r_6$ and $r_7$ are each independently hydrogen, alkyl, lower alkoxy, lower alkylthio lower alkyl, lower alkoxycarbonyl or benzyl; $r_1$ is lower alkyl optionally substituted by hydrogen or lower alkoxy, acetyl or lower alkenyl; $r_2$ is hydrogen or methyl; $r_3$ and $r_4$ are each independently hydrogen, halogen, hydroxy, lower alkyl or lower alkoxy; $r_5$ is lower alkyl optionally substituted by hydrogen or hydroxy; or $r_4$ may form in together with $r_5$ a bond, such as —CH$_2$—, —CH$_2$CH$_2$— and —OCH$_2$—; and ――――― represents a single bond or a double bond, and pharmaceutically-compatible complexes thereof are disclosed, and wherein it is described that these compounds and complexes have (1) an excellent cardiotonic effect and therefore can be a therapeutic drug for congestive heart failure and (2) a preventive effect on platelet aggregation.

DISCLOSURE OF THE INVENTION

The inventors of the present invention had investigated on compounds represented by the general formula [I] or the pharmaceutically-compatible complexes thereof for aiming at developing their novel medical use. As the result, the inventors found that compounds represented by the general formula [I], which is a compound group of the compounds represented by a general formula [II] wherein $r_1$ is $C_3H_7$, or the pharmaceutically-compatible complexes thereof have an excellent preventive effect on platelet aggregation and less cardiotonic effect, and they can be used as an preventive agent for platelet aggregation. It is an unexpected fact that the compounds represented by the general formula [I] or the pharmaceutically-compatible complexes thereof have less cardiotonic effect, basing upon the prior knowledge in the art on the compounds represented by the general formula [II] or the pharmaceutically-compatible complexes thereof.

It is an object of the present invention to provide an excellent preventive agent for platelet aggregation, which comprises a compound represented by the following general formula [I]:

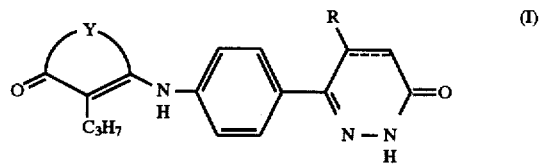

wherein Y is —CH$_2$CH$_2$— or —CH$_2$CH$_2$CH$_2$ —, R is hydrogen or methyl and ――――― represents a single bond or a double bond, or a pharmaceutically-compatible complex thereof as the active ingredient and gives less side effect.

The compounds represented by the general formula [I] and the pharmaceutically-compatible complexes thereof can be manufactured according to a method disclosed in the Japanese Patent Laid-opened No. Hei 2-56468, which corresponds to U.S. Pat. No. 5,110,925.

Representative compounds for the compounds and the complexes are shown in Table 1.

TABLE 1

Structural Formula

| Compound No. | Y | R | ==== | Physical Data m.p. °C. |
|---|---|---|---|---|
| 1 | —CH$_2$CH$_2$CH$_2$— | H | Single bond | 222–225 |
| 2, 2' | —CH$_2$CH$_2$CH$_2$— | CH$_3$ | Single bond | 95–100 (173–176) |
| 3 | —CH$_2$CH$_2$— | H | Single bond | 165–167 |

In addition to the representatives above, in the compounds represented by the general formula [I], pyridazinol exists in the place of pyridazine, and the tautomers, such as enol form and keto form as represented by the following formulas,

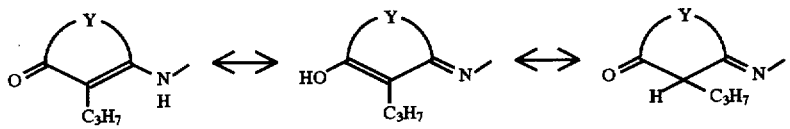

exist at the place of cycloalkenylamino group. Moreover, the optical isomers of pyridazinone also exists when R is methyl and ——————— represents a single bond.

It should be noted that the compounds according to the present invention include all isomers as described above.

The compounds represented by the general formula [I] or the pharmaceutically-compatible complexes thereof can be administrated into humans and animals in a form as they stand or with pharmaceutically-acceptable carriers customarily used. There is no limitation in the prescription form for the compounds and the complexes, and it is possible to select any prescription forms depending upon requirements. For the examples of the prescription forms, oral drugs such as tablets, granules and oral solution, parenteral drugs such as injection can be exemplified. Also, there is no particular limitation in the dose of the active ingredient to be administrated, and the dose can be properly determined out of the wide range depending on the prescription form, compounds selected, and humans or animals having the administration, however, it is preferable to dose the compound in an amount of from 0.06 to 10 mg/Kg/Day in order to demonstrate a desired effect. Futhermore, it is preferable to incorporate the active ingredient in an amount of from 1 to 500 mg in an unit prescription form.

In the present invention, oral drugs comprising the compound of the present invention, such as tablets, capsules and oral solution, can be prepared according to methods customarily used. For the preparation of the tablets, the compound represented by the general formula [I] or the pharmaceutically-compatible complex thereof is mixed with pharmaceutically-acceptable fillers, such as starch, lactose, gelatin, magnesium stearate, talc and gum arabic to form to tablets. For the preparation of the capsules, the compound represented by the general formula [I] or the pharmaceutically-compatible complex thereof is mixed with inactive pharmaceutically-acceptable fillers or diluents and then filled into hard gelatin capsules, soft capsules, etc. For the preparation of the medicated syrups or the elixirs, the compound represented by the general formula [I] or the pharmaceutically-compatible complex thereof is mixed with sweetners such as sucrose, antiseptics such as methyl- and propyl-paraben, coloring agents and flavorings. For the preparation of the parenteral drugs comprising the compound represented by the general formula [I] or the pharmaceutically-compatible complex thereof, a method customarily used can be employed. More specifically, the compound represented by the general formula [I] or the pharmaceutically-compatible complex thereof is dissolved into sterilized liquid carrier to prepare a drug for parenteral administration use. For the liquid carrier, it is preferable to use water or saline solution. For the preparation of liquid-form pharmaceuticals which have a desired transparency and stability and is usable for parenteral use, the active ingredient in an amount of from 1 to 500 mg is dissolved into either water or an organic solvent, then the solution is further dissolved into polyethylene glycol of which molecular weight is in a range of from 200 to 5000. In the liquid-form pharmaceuticals, it is preferable that a lubricant, such as polyvinyl pyrrolidone, polyvinyl alcohol, carboxymethyl-cellulose sodium and methylcellulose, is contained therein. In addition thereto, it is possible to add antiseptics, such as benzyl alcohol, phenol and thimerosal, and fungicides. Moreover, tonicity agents, such as sucrose and sodium chloride, local anesthetics, stabilizing agents, buffer agents, etc. can be added therein, if required. For improving the stability of the pharmaceuticals for parenteral use, it is possible to freeze the pharmaceuticals after the filling and then to remove water therefrom by using lyophilization technique which has been known in the art. Using the pharmaceuticals prepared in this way, the preparation of the lyophilized-powder just prior to the use can be realized.

BEST MODE FOR CARRYING OUT THE INVENTION

Now, the present invention is further explained with refferring to the following Examples.

[Reference Example 1]

Synthesis of 4,5-dihydro-6-[4- [(2-propyl-3-oxo-1-cyclohexenyl)amino] phenyl]-3(2H)-pyridazine (Compound No. 1)

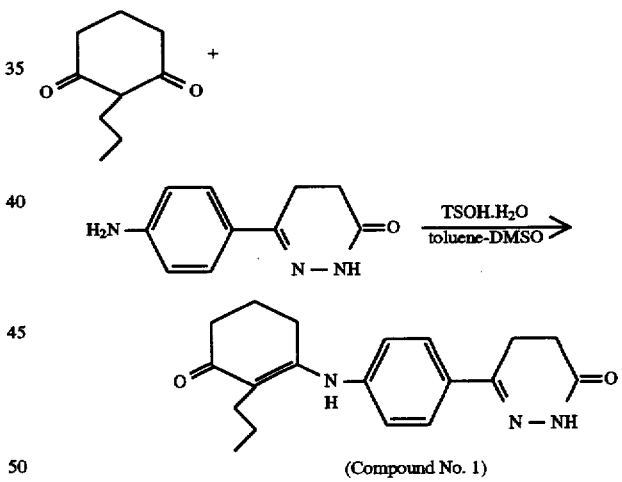

(Compound No. 1)

To a mixture of 10 ml toluene and 1 ml DMSO were dissolved 0.46 g of 4,5-dihydro-6-(4-aminophenyl)-3(2H)-pyridazinone and 0.1 g of p-toluenesulfonic acid, then the solution was subjected to a reflux for 2 hours while distillating water therein by using Dean-stark. After cooling the solution subjected to reflux, the solution was added with ether for the decantation, and the residue was purified by using silica gel column chromatography (Eluted used; A mixed solution of methanol:chloroform at a rate of 1:9) to obtain 0.55 g of the objective product. The melting point thereof was in a range of from 222° to 225° C.

[Reference Example 2]

Synthesis of 4,5-dihydro-5-methyl-6-[4-[(2-propyl-3-oxo-1-cyclohexenyl) amino]phenyl]-3(2H)-pyridazinone (Compound No. 2 and 2)

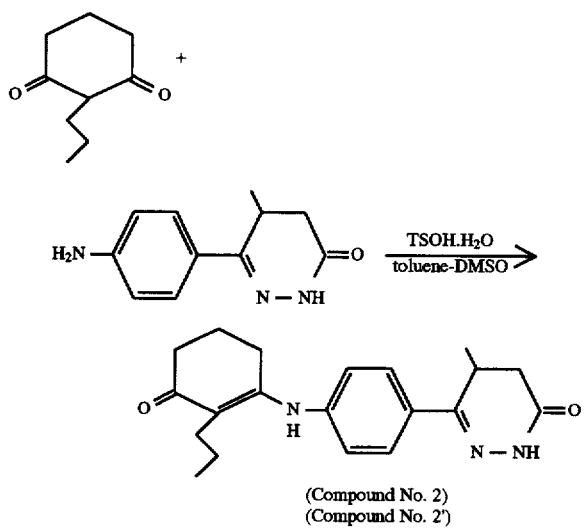

(Compound No. 2)
(Compound No. 2')

According to the same procedure as described in the Reference Example 1 except replacing 4,5-dihydro-6-(4-aminophenyl)-3(2H)-pyridazinone with 4, 5-dihydro-6-(4-aminophenyl)-6-methyl-3(2H)-pyridazine, a synthesis was carried out to obtain the objective compound (Compound No. 2) of which melting point is in a range of from 95° to 100° C. However, the melting point of the crystals of the objective product differed to a range of from 173° to 176° C. when the purification of the product was carried out by using silica gel column chromatography with using a different elute (A mixture if ethyl acetate and hexane at a rate of 1:1), to which Compound No. 2 is given.

EXAMPLE 1

Tablets

| Component | Quantity (g) |
| --- | --- |
| Compound No. 1 | 5 |
| Lactose (JP) | 50 |
| Corn starch (JP) | 25 |
| Crystalline cellulose (JP) | 25 |
| Methyl cellulose (JP) | 1.5 |
| Magnesium stearate (JP) | 1 |

Compound No. 1, lactose, corn starch and crystalline cellulose were thoroughly mixed, then the mixture was prepared to granules with using 5% aqueous solution of methyl cellulose. Then the granules were sieved through 200 mesh, then dried carefully. The granules dried were then sieved again through 200 mesh, mixed with magnesium stearate, and pressed to prepare the tablets. With the granules prepared as described above, 1,000 tablets for oral use were prepared.

EXAMPLE 2

Capsules

| Component | Quantity (g) |
| --- | --- |
| Compound No. 1 | 10 |
| Lactose (JP) | 80 |

-continued

| Component | Quantity (g) |
| --- | --- |
| Starch (JP) | 30 |
| Talc (JP) | 5 |
| Magnesium stearate (JP) | 1 |

Each components described above were separately pulverized to the fine powders, then all components were mixed and stirred to obtain an homogeneous mixture. The mixture was then filled into gelatin capsules in a desired size to be used for the parenteral administration. With the mixture prepared as described above, 1,000 pieces of two-piece type hard capsules for the oral use were prepared.

EXAMPLE 3

Injection

| Component | Quantity (g) |
| --- | --- |
| Compound No. 1 | 1 |
| Polyethylene glycol (JP) (Molecular weight: 4000) | 0.3 |
| Sodium chloride (JP) | 0.9 |
| Polyoxyethylene sorbitan oleate (JP) | 0.4 |
| Sodium meta-bisulfite | 0.1 |
| Methyl-paraben (JP) | 0.18 |
| Propyl-paraben (JP) | 0.02 |
| Distillated water for Injection | 100 (ml) |

The parabens, sodium meta-bisulfite and sodium chloride described above were dissolved into approximately 50 ml of distillated water at 80° C. with stirring. The solution obtained was cooled to 40° C., then compound No. 1 and subsequently polyethylene glycol and polyoxyethylene sorbitan monooleate were dissolved into the solution. Then sterilized water for injection was added into the solution up to the final objective volume of the solution. The solution was then subjected to a filtration using filter paper for the sterilization, then a sterilized solution adequate for the parenteral administration was prepared.

EXAMPLE 4

Capsules

| Component | Quantity (g) |
| --- | --- |
| Compound No. 1 | 10 |
| Lactose (JP) | 80 |
| Starch (JP) | 30 |
| Talc (JP) | 5 |
| Magnesium stearate (JP) | 1 |

Each components described above were separately pulverized to the fine powders, and all components were mixed and stirred to obtain an homogeneous mixture. The mixture was then filled into gelatin capsules in a desired size to be used for the parenteral administration. With the mixture prepared as described above, 1,000 pieces of two-piece type hard capsules for the oral use were prepared.

Industrial Applicability

Test Example 1

Preventive Effect on Platelet Aggregation

The preventive effect on platelet aggregation of the compounds and the complexes of the present invention was evaluated in vitro based on the preventive effect on the platelet aggregation induced by adenosine diphosphate (ADP) and collagen, which is determined by using an aggregometer, Hematracer PAT-606 produced by Nicho Bioscience Co., Ltd. Blood collected from rabbits containing 0.38% citric acid was centrifuged at 1100 rpm for 15 min. to obtain platelet rich plasm (PRP). The PRP obtained was then centrifuged at 3500 rpm for 10 min., and the supernatant obtained was provided as platelet poor plasma (PPP). PRP was diluted with PPP to adjust the concentration of platelets in PRP to a range of from $2\times10^8$ /ml to $5\times10^8$ ml. [Either ADP at the final concentration of 10 µM or collagen at the final concentration of 20 µg/ml, which was prepared with SKF buffer solution (Collagen reagent Horm, Hormon Chemie) was used for the induction of platelet aggregation.] Test compound was dissolved into dimethyl sulfoxide (DMSO), then 0.5 ml of PRP prepared as described above was added to 0.5 µl of the solution, then mixed for about 3 min. Then, 0.2 ml portion was taken out of the mixture, and either ADP solution or collagen solution in an amount of 22 µl was added thereto to proceed to the measurement of platelet aggregation for 10 min. by using an aggregometer. The preventive effect on platelet aggregation was determined in the prevention rate (%) in respect to the aggregation rate in the check plot. The rate of prevention onto platelet aggregation was calculated according to the following equation.

Platelet Aggregation Prevention Rate (%)=(Maximum Aggregation Rate(%) of Platelet when only DMSO is added−Maximum Aggregation Rate(%) of Platelet when Test Compound and DMSO are added)÷Maximum Aggregation Rate(%) of Platelet when only DMSO is added Based on the dose-response curve obtained according to the equation described above, $EC_{50}$, a dose attaining 50% prevention of platelet aggregation, was determined. The results are shown in Table 2.

TABLE 2

| Compound No. | $EC_{50}$ (µM) for Platelet Aggregation Prevention | |
|---|---|---|
| | ADP | Collagen |
| 1 | 29.8 | 9.3 |
| 2 | 4.5 | 3.6 |
| 3 | 22.8 | 12.9 |
| Cilostazol | 10.2 | 4.3 |

Test Example 2

Preventive Effect on Thrombus-causing Death

Mice in a state without feeding for a night were orally administrated with a test compound, and then injected intravenously with collagen in an amount of 400 µg/Kg and epinephylline in an amount of 50 µg/Kg through their tail at a fixed speed in accordance with the method of DiMinno and Silver (DiMinno, G. and Silver, M. J.. J. Pharmacol. Exp. Thor., 225, 57–60, 1983). After 30 min., the mice were checked to determine their survival rate and to calculate $EC_{50}$, a dose attaining 50% prevention of the death of the mice. The collagen and epinephylline were used in a form of a mixed solution prepared with SKF buffer solution and saline, respectively. Test compounds were administrated to mice after preparing each suspensions of the compounds in 1% aqueous solution of gum arabic.

(Note) J. Pharmacol. Exp. Ther. : The Journal of Pharmacology and Experimental Therapeutics The results are shown in Table 3.

TABLE 3

| Compound No. | $ED_{50}$ (mg/Kg, p.o.) for preventing Thrombus-causing Death |
|---|---|
| 1 | 5.0 |
| 2 | 1.7 |
| 3 | 6.8 |
| Cilostazol | 300 |

Test Example 3

Inhibitory Effect on Phosphodiesterase

Cyclic guanosine monophosphate inhibiting-type cyclic adenosine monophosphate phosphodiesterase (cAMP-PDE) derived from canine platelets was prepared according to the method of Thompson et. al. (Thompson, W. J., et. al., Adv. Cyclic Nucleotide Res., 10, 69–92, 1979).

More specifically, the canine platelets specimen was subjected to an elution by employing Concentration Gradient on DEAE-Cellulose column chromatography (Produced by Whatman Inc., Type BE-52, Diameter 3.2 cm, Length 13 cm) using 70 to 1000 mM of sodium acetate as an elute to separate the esterage.

The phosphodiesterase activity was measured according to the method of Thompson et. al. which was partially modified by the inventors of the present invention. Namely, 1 µM [$^3$H]-cAMP was decomposed with phosphodiesterase, then 5'-AMP resulted was subjected to snake venom (Produced by Sigma, V-7000) to degrade it to adenosine. The resulting solution was added into anion-exchange resin (Produced by Bio-rad, AG1-X8), and adenosine as the reaction product and unreacted cAMP were separated by an extraction with methanol, then unadsorped adenosine to the resin was measured by using a liquid scintillation counter. Based on the concentration-inhibition curve prepared, $IC_{50}$, a concentration attaining 50% inhibition of enzymatic activity, was determined.

(Note) Adv. Cyclic Nucleotide Res.; Advances in Cyclic Nucleotide Research

The results are shown in Table 4.

TABLE 4

| Compound No. | $IC_{50}$ (µM) for cAMP-PDE |
|---|---|
| 1 | 0.43 |
| 2 | 0.088 |
| 3 | 0.37 |
| Cilostazol | 0.60 |

Test Example 4

Cardiotonic Effect

Male and female Beagle dogs in a weight range of from 10 to 15 Kg were anesthetized to provide them for the test. The dogs were anesthetized by intravenous injection with sodium pentobarbital at a dose of 30 mg/Kg/hr, and the anesthetized condition was maintained by subsequent intravenous injection with sodium pentobarbital at a dose of 4 mg/Kg/hr. A cannula for drip infusion either of physiological saline solution or anesthetic injection was inserted into a femoral vein, and a cannula for measuring arterial blood pressure was inserted into a femoral artery via a pressure transducer. Heart rate was recorded by conducting R-wave of the electrocardiogram (ECG) to a heart beat counter.

Secondary induction from electrocardiogram was measured via a bioelectricity-adapted amplifier. Internal pressure of left cardiac ventricle was measured by inserting a catheter-type pressure transducer from a left carotid into left cardiac ventricle. Differential values by time of the internal pressure in left cardiac ventricle (dp/dt max) were measured by conducting the internal pressure in left cardiac ventricle to a derivative amplifier. The test compound was cummulatively administrated at a rate of from 0.001 to 0.3 mg/0.1 ml/Kg though a cannula inserted into a femoral vein. Based on a dose-response curve obtained, $ED_{50}$, a dose attaining 50% increase of the dp/dt max in left cardiac ventricle, was determined.

The results are shown in Table 5.

TABLE 5

| Compound No. | $ED_{50}$ (μg/Kg. i.v.) for dp/dt max in Left Cardiac Ventricle | % Change Heart Rate | Blood pressure |
| --- | --- | --- | --- |
| 1 | >300(32%)* | (5.2%)* | (−8.6%)* |
| 2 | 52 | 9.8 | −10.0 |
| 3 | 100 | 7.5 | −10.5 |
| Cilostazol | 200 | 15 | −2.1 |

*% Change in intravenous administration at 300 mg/Kg.

The test according to Test Example 1,2,3 and 4 was also carried out on compound No. 2'(m.p. 173°–176° C.), and it was found that the effects of the compound were as much as the effects given by the compound No. 2.

What is claimed is:

1. A preventive agent for platelet aggregation comprising an effective amount of 4,5-dihydro-5-methyl-6-[4-[(2-propyl-3-oxo-1-cyclohexenyl) amino]phenyl]-3(2H)-pyridazinone and a pharmaceutically acceptable excipient or carrier.

* * * * *